(12) United States Patent
Granqvist et al.

(10) Patent No.: US 8,483,611 B2
(45) Date of Patent: Jul. 9, 2013

(54) COMMUNICATION BETWEEN PORTABLE APPARATUS AND COUNTERPART APPARATUS

(75) Inventors: Niclas Granqvist, Fleurier (CH); Juhani Kemppainen, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 13/569,474

(22) Filed: Aug. 8, 2012

(65) Prior Publication Data

US 2012/0302165 A1 Nov. 29, 2012

Related U.S. Application Data

(62) Division of application No. 12/401,023, filed on Mar. 10, 2009.

(30) Foreign Application Priority Data

Apr. 3, 2008 (FI) ...................................... 20085280

(51) Int. Cl.
*H04B 5/00* (2006.01)
(52) U.S. Cl.
USPC ........................................... 455/41.1; 607/60
(58) Field of Classification Search
USPC .................... 455/456.3, 440, 121, 41.2, 41.3, 455/410–411, 415, 558; 607/60
See application file for complete search history.

(56) References Cited

U.S. PATENT DOCUMENTS

| 4,625,733 A | 12/1986 | Saynajakangas |
|---|---|---|
| 5,611,346 A | 3/1997 | Heikkila et al. |
| 5,632,279 A | 5/1997 | Heikkila |
| 6,892,052 B2 | 5/2005 | Kotola et al. |
| 7,181,505 B2 * | 2/2007 | Haller et al. ................... 709/219 |
| 7,292,867 B2 * | 11/2007 | Werner et al. ............... 455/456.3 |
| 7,565,108 B2 * | 7/2009 | Kotola et al. ................ 455/41.2 |
| 7,643,895 B2 | 1/2010 | Gupta et al. |
| 7,711,375 B2 | 5/2010 | Liu |
| 2003/0065536 A1 | 4/2003 | Hansen et al. |
| 2004/0234000 A1 | 11/2004 | Page |
| 2005/0134451 A1 | 6/2005 | Nikkola |
| 2006/0004294 A1 | 1/2006 | Juntunen et al. |
| 2007/0202807 A1 | 8/2007 | Kim |
| 2008/0146265 A1 | 6/2008 | Valavi |

FOREIGN PATENT DOCUMENTS

| DE | 20216591 U1 | 1/2003 |
|---|---|---|
| EP | 0747003 A1 | 12/1996 |
| WO | WO2005083947 A1 | 9/2005 |

OTHER PUBLICATIONS

"Wireless Medium Access Control (MAC) and Physical Layer (PHY) Specifications for Low-Rate Wireless Personal Area Networks (LR-WPANs)", IEEE Standard 802.15.4-2003, pp. 1-63 (2003).

* cited by examiner

*Primary Examiner* — Dinh T. Le
(74) *Attorney, Agent, or Firm* — Hoffmann & Baron, LLP

(57) ABSTRACT

A portable apparatus, a counterpart apparatus and communication method are disclosed. The communication method comprises: communicating wirelessly an identifier from a portable apparatus to a counterpart apparatus by an induction-based magnetic field; executing a pairing protocol utilizing the identifier between the radio transceiver of the portable apparatus and a radio transceiver of the counterpart apparatus by electric radiation; and communicating information between the radio transceiver of the portable apparatus and the radio transceiver of the counterpart apparatus by electric radiation.

9 Claims, 2 Drawing Sheets

COMMUNICATION BETWEEN PORTABLE APPARATUS AND COUNTERPART APPARATUS

CROSS-REFERENCE TO RELATED APPLICATIONS

This application is a divisional of U.S. application Ser. No. 12/401,023, filed Mar. 10, 2009, which claims priority based on Finnish Patent Application No. 20085280, filed Apr. 3, 2008, both of which are incorporated herein by reference.

BACKGROUND

1. Field

The invention relates to a portable apparatus, a counterpart apparatus, and a communication method.

2. Description of the Related Art

A portable apparatus, such as a heart rate monitor, may communicate information, such as heart activity data, to a counterpart apparatus, such as an exercise apparatus, over a radio link. In order to be able to communicate, the radio transceivers of the portable apparatus and the counterpart apparatus need first to be paired together. This is achieved by executing a pairing protocol. However, as there may be many portable apparatuses present, and possibly also many counterpart apparatuses may be present, it may be problematic to find out which portable apparatus wishes to be paired together with a specific counterpart apparatus.

SUMMARY

The present invention seeks to provide improvements in the communication between a portable apparatus and a counterpart apparatus.

According to an aspect of the present invention, there is provided a portable apparatus as specified in claim 1.

According to another aspect of the present invention, there is provided a counterpart apparatus as specified in claim 8.

According to another aspect of the present invention, there is provided a communication method as specified in claim 9.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1:
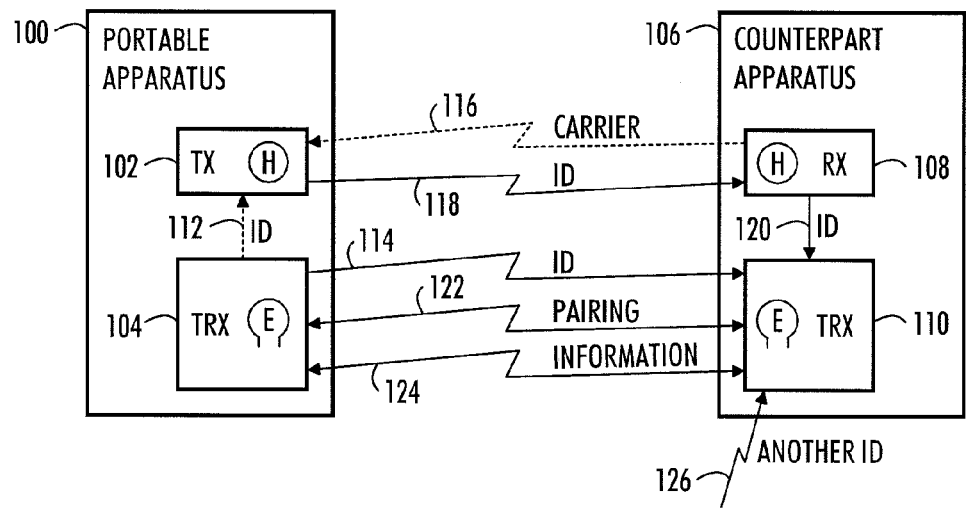
FIG. 1 illustrates a portable apparatus and a counterpart apparatus.

FIG. 1 illustrates a portable apparatus 100 and a counterpart apparatus 106. FIG. 1 is a simplified block diagram that only shows some elements and functional entities, all being logical units whose implementation may differ from what is shown. The connections shown in FIG. 1 are logical connections; the actual physical connections may be different. It is apparent to a person skilled in the art that the described apparatuses 100, 106 may also comprise other functions and structures. It should be appreciated that some functions, structures, and elements, and the protocols used for communication are irrelevant to the actual invention. Therefore, they need not be discussed in more detail here. The specifications of apparatuses 100, 106 develop rapidly. Such development may require extra changes to an embodiment. Therefore, all words and expressions should be interpreted broadly and they are intended to illustrate, not to restrict, the embodiments. Although the apparatuses 100, 106 have been depicted as separate single entities, different parts may be implemented in one or more physical or logical entities.

The term 'portable apparatus' 100 may refer to a complete device that a user is capable of carrying around, or to a part of such a device. The complete device 100 may be a heart rate monitor, a heart rate transmitter wearable on the chest of a user, a personal measurement device, a wrist-worn measurement device, or a subscriber terminal of a radio system, for example. A part of such a device 100 may be an electronic circuit implementing the described behavior of the portable apparatus 100 embodiments. The electronic circuit may comprise logic components, standard integrated circuits, and/or application-specific integrated circuits (ASIC).

The term 'counterpart apparatus' 106 may refer to a complete device capable of interacting with the portable device 100, or to a part of such a device. The complete device 106 may be a computer, an exercise apparatus, or a health club apparatus, for example. A part of such a device 106 may be an electronic circuit implementing the described behavior of the counterpart apparatus 106 embodiments. The computer may be a personal computer (such as a desktop computer, a laptop computer, or a palmtop computer). The computer may also be a server computer. The computer may store and process heart activity data of countless persons. The computer may be team specific, i.e. it is used to process the heart activity data of a certain team. Alternatively, the computer may provide heart activity data storage and analysis services to a wide audience, as a world-wide web (WWW) server over the Internet, for example. If the counterpart apparatus 106 is an exercise apparatus, such as a treadmill, the training load may be regulated, a diary may be stored, etc. utilizing the communication to be described later on.

The portable apparatus 100 comprises two communication devices: an induction-based transmitter 102 and a radio transceiver 104. Correspondingly, the counterpart apparatus 106 comprises an induction-based receiver 108 and a radio transceiver 110.

Consequently, two different wireless communication technologies are used: induction-based technology utilizing a magnetic field, and a radio-based technology utilizing electric radiation. It is to be noted that both technologies involve both the magnetic field and the electric radiation, but the separation is based on the fact that either one of these physical phenomena predominates and is only used for the communication in each technology.

A crucial difference between these two communication technologies is the signal attenuation as a function of the length of a signal propagation path. In the induction-based communication technology, the signal level is inversely proportional to the third power of the length of the signal propagation path, whereas in the radio-based technology, the signal level is inversely proportional to the second power of the length of the signal propagation path. This results in a dramatic difference in the spatial sensitivity of the communication and means that with the induction-based technology it is possible to recognize the portable apparatus 100 that wants to pair with the counterpart apparatus 106, whereupon the actual pairing may be performed with the radio-based technology. A typical coverage of the induction-based communication is of the order of human dimensions, i.e. about 1.5 meters.

The induction-based transmitter 102 may be a kilohertz-range transmitter, a passive radio-frequency identification tag, or a near field communication transmitter, for example. Correspondingly, the induction-based receiver 108 may be a kilohertz-range receiver, a radio-frequency identification tag reader, or a near field communication receiver, for example. The kilohertz-range transmission may operate at 5-kilohertz frequency, for example. Higher frequencies, such as those exceeding 200 kilohertz, may also be possible. In an embodiment, the kilohertz-range includes 125 kilohertz. Near field communication may refer to a short-range high frequency wireless communication technology, known also as NFC, which enables communication over about a 10-centimeter distance.

The radio transceiver 104, 110 may be a proprietary transceiver, or a Bluetooth transceiver, for example. Emerging ultra low power Bluetooth technology may be used, as its expected use cases include heart rate monitoring. The proprietary radio transmission may operate at 2.4-gigahertz frequency, for example.

Next, the communication between the portable apparatus 100 and the counterpart apparatus 106 is described as a communication sequence 112-114-116-118-120-122-124. The communication sequence described in FIG. 1 is in no absolute chronological order. Other functions, not described in this application, may also be executed within the sequence. Some parts of the sequence may also be left out or replaced by a corresponding part.

An identifier, associated with the radio transceiver 104 of the portable apparatus 100, needs to be known by the induction-based transmitter 102 of the portable apparatus 100. This may be implemented in any suitable way: the identifier is communicated 112 during the use of the portable apparatus 100 from the wireless transceiver 104 to the induction-based transmitter 102, for example. This communication 112 may be implemented with suitable interface technologies, such as a message interface, method interface, sub-routine call interface, block interface, or any means enabling communication between functional sub-units. Another possibility is that the identifier is programmed in a memory of the induction-based transmitter 102 during manufacture or service of the portable apparatus 100.

The radio transceiver 104 of the portable apparatus 100 may be configured to provide 114 its identifier to the radio transceiver 110 of the counterpart apparatus 106. However, this is not enough: as was explained in the Background section, there may be many portable apparatuses operating simultaneously and transmitting their identifiers, and as result of this, the counterpart apparatus 106 does not know with which portable apparatus it should be paired with. Picture the following scenario in a health club: a user armed with the portable apparatus 100 wishes to exercise with the counterpart apparatus 106, but the counterpart apparatus 106 cannot decide whether it should be paired with the identifier 114 transmitted by the portable apparatus 100 or with another identifier 126 transmitted by another portable apparatus.

For that reason, the induction-based transmitter 102 of the portable apparatus 100 is configured to wirelessly provide 118 the identifier to the counterpart apparatus 106 by a magnetic field, and the induction-based receiver 108 of the counterpart apparatus 108 is configured to wirelessly obtain 118 the identifier from the portable apparatus 100 by the magnetic field.

In an embodiment, the counterpart apparatus 106 may first transmit 116 a magnetic field as a carrier to the portable apparatus 100, whereupon the portable apparatus 100 may modulate this carrier in order to transmit 118 the identifier to the counterpart apparatus 106. In that case, the induction-based receiver 108 of the counterpart apparatus 106 also comprises a transmitter (not illustrated in FIG. 1) configured to transmit the carrier. Such an embodiment may resemble reading of a passive RFID tag/transponder, where reading distances may vary from ten centimeters up to a few meters.

As illustrated in FIG. 1, the identifier received by the counterpart apparatus 106 is then provided 120 from the induction-based receiver 108 to the radio transceiver 110 of the counterpart apparatus 106. This communication 120 may be implemented with suitable interface technologies, such as a message interface, method interface, sub-routine call interface, block interface, or any means enabling communication between functional sub-units.

Now that the counterpart apparatus 106 knows with which portable apparatus 100 it needs to execute the pairing protocol, the next part of the sequence may be performed. The radio transceiver 104 of the portable apparatus 100 associated with the identifier is configured to execute 122 the pairing protocol utilizing the identifier with the counterpart apparatus 106 by electric radiation, and the radio transceiver 110 of the counterpart apparatus 106 is configured to execute 122 the pairing protocol utilizing the identifier with the portable apparatus 100 by electric radiation.

Having been paired together, the portable apparatus 100 and the counterpart apparatus 106 may now proceed to the last part of the sequence. The radio transceiver 104 of the portable apparatus 100 is configured to communicate 124 information with the counterpart apparatus 106 by electric radiation, and the radio transceiver 110 of the counterpart apparatus 106 is configured to communicate 124 information with the portable apparatus 100 by electric radiation. The information may be any data that the portable apparatus 100 and the counterpart apparatus 106 need to communicate to each other. The information may be specific to a user of the portable apparatus 100, specific to the portable apparatus 100, or specific to the counterpart apparatus 106. The information may be heart activity data, which may include heart rate information, beat-to-beat intervals, and/or an electrocardiogram (ECG), for example. Other possible information include heart rate limits, calorie information, body temperature of the user, status of the battery of the portable apparatus 100, training schedules, equipment identification information, user information, registration information, etc.

The identifier associated with the radio transceiver 104 of the portable apparatus 100 may be any identifier used in the pairing protocol. The term 'pairing protocol' refers here to any protocol that is used in ad hoc based communication to recognize the parties of the communication. The identifier may be a medium access control (MAC) address of the radio transceiver 104, or a part of a medium access control address of the radio transceiver 104. Bluetooth utilizes such MAC addresses, for example.

Table 1 describes a unique 48-bit Bluetooth device address (LSB=Least significant bit, MSB=Most significant bit). Such an address may be obtained from the IEEE Registration Authority. The device address comprises two main fields: a company_id field, and a company_assigned field. The company_id field comprises two fields: UAP field and NAP field. The company_assigned field comprises only one field: LAP field.

TABLE 1

| Bluetooth device address (BD_ADDR) | | | | | | | | | | | |
|---|---|---|---|---|---|---|---|---|---|---|---|
| LSB | | | | | | | | | | | MSB |
| company_assigned | | | | | | company_id | | | | | |
| LAP | | | | | | UAP | | NAP | | | |
| 0000 | 0001 | 0000 | 0000 | 0000 | 0000 | 0001 | 0010 | 0111 | 1011 | 0011 | 0101 |

As was earlier described in connection with the communication sequence, the radio transceiver 104 of the portable apparatus 100 may be configured to provide 114 its identifier to the radio transceiver 110 of the counterpart apparatus 106. In Bluetooth, this may be performed in a so-called promiscuous mode. This has an effect that the radio transceiver 110 of the counterpart apparatus 106 knows all identifiers of those portable apparatuses that are within the reception range. For that reason, it may be so that only a part of the MAC address needs to be transmitted 118 as an identifier by the induction-based transmitter 102 of the portable apparatus 100. The induction-based transmitter 102 may be configured to wirelessly provide 118 a predetermined number of the least significant bits of the medium access control address of the radio transceiver 104, and the induction-based receiver 108 may be configured to wirelessly receive 118 the predetermined number of the least significant bits of the medium access control address of the radio transceiver 104.

Let us take three example addresses, from which only the 16 least significant bits are shown:
 address 1: 01101010 10101011;
 address 2: 11001101 1̄0̄1̄0̄1̄0̄0̄0̄; and
 address 3: 11001 1̄0̄1̄ 00000000.

The predetermined number of the least significant bits could be 7 bits, for example. The first of these bits may start after the first bit that has the value one starting from the least significant bit. These bits are in bold and they are underlined in the example addresses.

Figure 2:
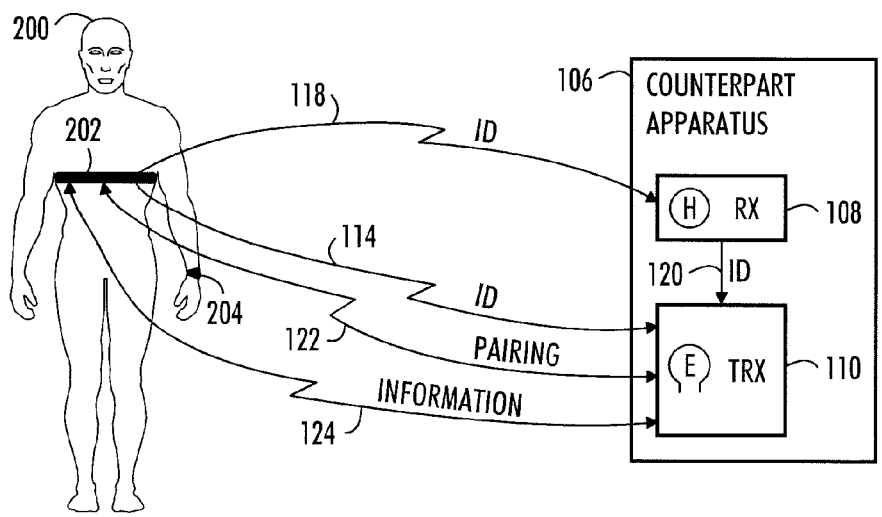
FIGS. 2, 3 and 4 illustrate various embodiments of a portable apparatus and a counterpart apparatus.
Figure 3:
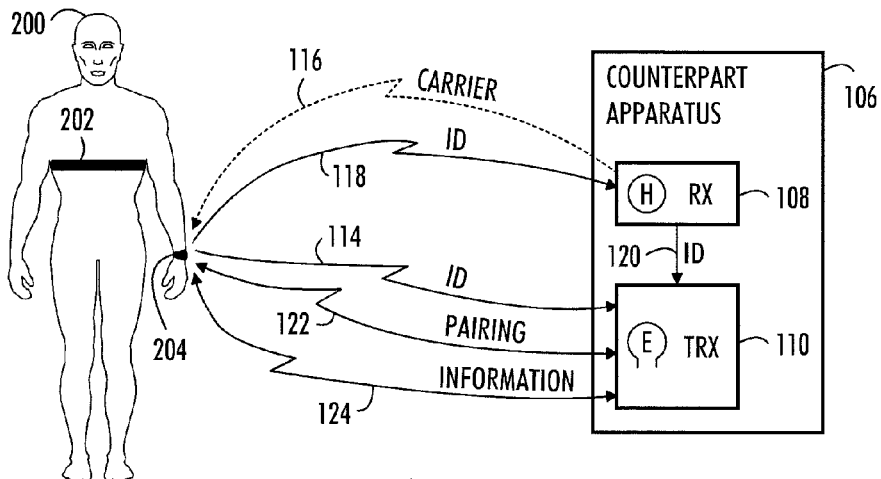
Figure 4:
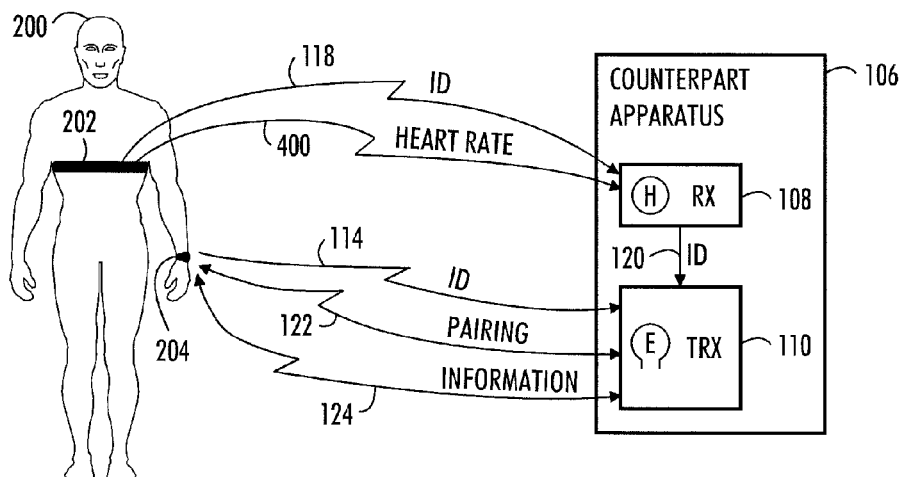

Next, FIGS. 2, 3 and 4 illustrate various embodiments of the portable apparatus 100 and the counterpart apparatus 106, wherein the portable apparatus 100 is implemented as a heart rate monitor. Polar Electro® (www.polarusa.com) designs and manufactures heart rate monitors and their accessories. At the time of filing this patent application, the apparatus may be implemented based on a Polar WearLink® transmitter W.I.N.D., which is a textile transmitter belt 202 worn around the chest of the user 200 to transmit heart activity data, and on a Polar RS800sd Running Computer, which is a user interface unit 204 of the heart rate monitor. The transmission of the heart activity data may utilize the principles of time division and/or packet transmission, for example.

The user interface unit 204 may be worn around the wrist, like a watch, but it may well be implemented to another kind of platform, such as a subscriber terminal of a radio system: a mobile telephone for example. The user interface unit 204 may also be a sports watch for use as an instrument in sports.

FIG. 2 describes an embodiment, wherein the heart rate transmitter 202 wearable on the chest of the user 200 comprises both the induction-based transmitter (=a kilohertz-range transmitter, for example) 102 and the radio transceiver (=a Bluetooth transceiver, for example) 104. First, the Bluetooth transceiver may transmit 114 its identifier (BD_ADDR, for example) to the counterpart apparatus 106. Next, the heart rate transmitter 202 may utilize the kilohertz-range transmitter to transmit 118 the identifier of the Bluetooth transceiver (7 bits of the BD_ADDR, as described above, for example) to the counterpart apparatus 106. The counterpart apparatus 106 is then able to identify the correct portable apparatus 100. The heart rate transmitter 202 (or to be precise, its Bluetooth transceiver) and the counterpart apparatus 106 may then be paired 122 with each other, whereupon information communication 124 may start.

FIG. 3 describes an embodiment, wherein the user interface unit 204 comprises both an induction-based transmitter (=a passive radio-frequency identification tag, for example) 102 and the radio transceiver (=a Bluetooth transceiver, for example) 104. First, the Bluetooth transceiver may transmit 114 its identifier (BD_ADDR, for example) to the counterpart apparatus 106. Next, the passive radio-frequency identification tag may provide 118 the identifier of the Bluetooth transceiver (BD_ADDR, or a part of it as described above, for example) to the counterpart apparatus 106. The earlier described carrier mechanism 116 may be used here as well. The counterpart apparatus 106 is then able to identify the correct portable apparatus 100. The user interface unit 204 (or to be precise, its Bluetooth transceiver) and the counterpart apparatus 106 may then be paired 122 with each other, whereupon information communication 124 may start.

FIG. 4 describes an embodiment, wherein the heart rate transmitter 202 wearable on the chest of the user 200 comprises the induction-based transmitter (=a kilohertz-range transmitter, for example) 102, and the user interface unit 204 comprises the radio transceiver (=a Bluetooth transceiver, for example) 104.

First, the Bluetooth transceiver may transmit 114 its identifier (BD_ADDR, for example) to the counterpart apparatus 106. Next, the heart rate transmitter 202 may utilize the kilohertz-range transmitter to transmit 118 the identifier of the Bluetooth transceiver (7 bits of the BD_ADDR, as described above, for example) to the counterpart apparatus 106.

The identifier may be transmitted as stand-alone information, or encoded within a stream of heart activity data. Encoding is described in two other patents of the applicant: U.S. Pat. Nos. 5,611,346 and 5,632,279.

As was explained earlier, the identifier may be associated with the radio transceiver 104 of the portable apparatus 100. However, other embodiments are also feasible. In an embodiment, the identifier is associated with the portable apparatus 100. The identifier may be any information which is transmitter both by the induction-based transmitter 102 and the radio transmitter 104. The counterpart apparatus 106 may compare the identifiers obtained from the radio transceivers with those obtained from the induction-based transmitter 102 and establish a connection or start data transfer with such a radio transceiver that transmits an identifier matching with an identifier communicated by the induction-based transmitter 102. In an embodiment, the identifier is an identifier of the induction-based transmitter 104. The identifier may define a transmission channel of the induction-based transmitter 102. The code space defining the possible identifiers of the transmission channel of the induction-based transmission may be rather limited. If the same code occurs twice or more frequently in the counterpart apparatus 106, the counterpart apparatus 106 may transmit an enquiry message to the portable apparatus 100 in order to obtain additional identifiers. Such identifiers may be based on heart rate information, such as time interval of successive heart pulses.

The counterpart apparatus 106 is then able to identify the correct portable apparatus 100. The user interface unit 204 (or to be precise, its Bluetooth transceiver) and the counterpart apparatus 106 may then be paired 122 with each other, whereupon information communication 124 may start.

It is to be noted that in this embodiment the heart rate transmitter 202 may continue to transmit 400 heart activity data.

It is to be noted that when the separate transmitter belt 202 and user interface unit 204 are used, the processing of the heart activity measurements may be distributed between the transmitter belt 202 and the user interface unit 204. The choice of the distribution depends on the processing power and power consumption requirements and on the transmission capacity, and it may have an effect on how the described communication is best implemented.

The implementation of the earlier described embodiments in such an existing product requires relatively small and well-defined modifications. Only the above-described communication needs to be implemented. Naturally, as the products evolve, the feasible platforms for the implementation of the embodiments described in this patent application also evolve and emerge.

Other implementations may also be possible. The heart rate monitor may also be implemented so that, instead of the solution comprising the transmitter belt 202 and the user interface unit 204, the heart rate may directly be measured from the wrist on the basis of the pressure, for example. Other ways for measuring the heart rate may also be employed. As sensor technology becomes more integrated, less expensive, and its power consumption characteristics are improved, the sensor measuring heart activity data may also be placed in other arrangements besides the transmitter belt 202. Polar Electro® is already marketing clothes that may be provided with separate small sensor units wirelessly communicating with the wrist unit 204.

The portable apparatus 100 may be a part of a heart rate monitor for measuring the user's heart rate and possibly other parameters that can be measured non-invasively (such as blood pressure). In U.S. Pat. No. 4,625,733, which is incorporated herein by reference, Säynäjäkangas describes a wireless and continuous heart rate monitoring concept where a transmitter to be attached to the user's chest measures the user's ECG-accurate (electrocardiogram) heart rate and transmits the heart rate information telemetrically to the heart rate receiver attached to the user's wrist by using magnetic coils in the transmission.

Figure 5:
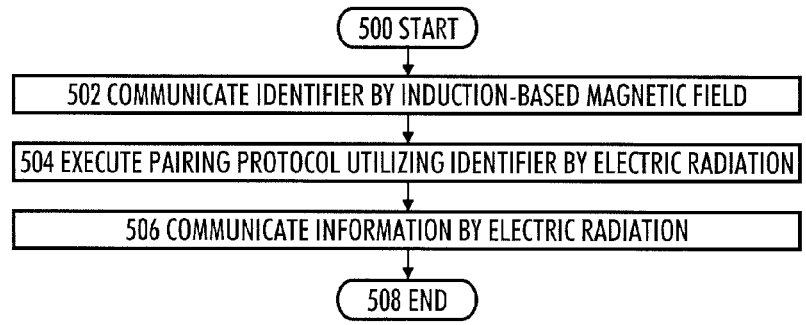
FIG. 5 is a flowchart illustrating an embodiment of a communication method.

Next, a communication method will be described with reference to FIG. 5. The operations described in FIG. 5 are in no absolute chronological order. Other functions, not described in this application, may also be executed between the operations or within the operations. Some of the operations or parts of the operations may also be left out or replaced by a corresponding operation or part of the operation. The method starts in 500. In 502, an identifier of a radio transceiver is wirelessly communicated from a portable apparatus to a counterpart apparatus by an induction-based magnetic field. In 504, a pairing protocol utilizing the identifier is executed between the radio transceiver of the portable apparatus and a radio transceiver of the counterpart apparatus by electric radiation. In 506, information is communicated between the radio transceiver of the portable apparatus and the radio transceiver of the counterpart apparatus by electric radiation. The method ends in 508. The above-described embodiments of the apparatuses may also be used to enhance the method.

As technology advances, the inventive concept can be implemented in various ways. The invention and its embodiments are not limited to the examples described above but may vary within the scope of the claims.

What is claimed is:

1. A counterpart apparatus comprising:
an induction-based receiver configured to wirelessly obtain an identifier from a portable apparatus by a magnetic field, the induction-based receiver being configured to wirelessly obtain heart activity data from the portable apparatus using induction-based technology in which the magnetic field is predominantly used to communicate the heart activity data; and
a radio transceiver coupled to the induction-based receiver and configured to execute a pairing protocol between the radio transceiver and the portable apparatus using radio-based technology in which electric radiation is predominantly used to execute the pairing protocol, the radio transceiver executing the pairing protocol using the identifier, the radio transceiver being configured to communicate information with the portable apparatus based on execution of the pairing protocol using the radio-based technology.

2. The counterpart apparatus of claim 1, wherein the induction-based receiver comprises a kilohertz-range receiver, a radio-frequency identification tag reader, or a near field communication receiver.

3. The counterpart apparatus of claim 1, wherein the radio transceiver comprises a proprietary transceiver, or a Bluetooth transceiver.

4. The counterpart apparatus of claim 1, wherein the identifier comprises an identifier associated with the radio transceiver of the portable apparatus, an identifier associated with the portable apparatus, an identifier of the induction-based transmitter, an identifier defining a transmission channel of the induction-based transmitter, a medium access control address of the radio transceiver, or a part of a medium access control address of the radio transceiver.

5. The counterpart apparatus of claim 4, wherein the induction-based receiver is configured to wirelessly receive a predetermined number of the least significant bits of the medium access control address of the radio transceiver.

6. The counterpart apparatus of claim 1, wherein the information comprises information specific to a user of the portable apparatus, information specific to the portable apparatus, or information specific to the counterpart apparatus.

7. The counterpart apparatus of claim 1, wherein the counterpart apparatus comprises an electronic circuit, a computer, an exercise apparatus, or a health club apparatus.

8. A counterpart apparatus comprising:
an induction-based receiver configured to wirelessly obtain an identifier from a portable apparatus by a magnetic field, the induction-based receiver being configured to wirelessly obtain the identifier encoded within a stream of heart activity data from the portable apparatus using induction-based technology in which the magnetic field is predominantly used to communicate the identifier and the heart activity data; and a radio transceiver coupled to the induction-based receiver and configured to execute a pairing protocol between the radio transceiver and the portable apparatus using radio-based technology in which electric radiation is predominantly used to execute the pairing protocol, the radio transceiver executing the pairing protocol using the identifier, the radio transceiver being configured to communicate information with the portable apparatus based on execution of the pairing protocol using the radio-based technology.

9. A counterpart apparatus comprising:
an induction-based receiver configured to wirelessly obtain an identifier from a portable apparatus by a magnetic field, the induction-based receiver being configured to wirelessly obtain heart activity data from the portable apparatus using induction-based technology in which the magnetic field is predominantly used to communicate the heart activity data; the counterpart apparatus comprising an exercise apparatus, or a health club apparatus; and
a radio transceiver coupled to the induction-based receiver and configured to execute a pairing protocol between the radio transceiver and the portable apparatus using radio-based technology in which electric radiation is predominantly used to execute the pairing protocol, the radio transceiver executing the pairing protocol using the identifier, the radio transceiver being configured to communicate information with the portable apparatus based on execution of the pairing protocol using the radio-based technology.

* * * * *